United States Patent [19]

Mault

[11] Patent Number: 5,179,958
[45] Date of Patent: * Jan. 19, 1993

[54] RESPIRATORY CALORIMETER WITH BIDIRECTIONAL FLOW MONITOR

[76] Inventor: James R. Mault, 4227 Pin Oak Dr., Durham, N.C. 27707

[*] Notice: The portion of the term of this patent subsequent to Aug. 6, 2008 has been disclaimed.

[21] Appl. No.: 726,922

[22] Filed: Jul. 8, 1991

Related U.S. Application Data

[63] Continuation-in-part of Ser. No. 368,947, Jun. 23, 1989, Pat. No. 5,038,792, which is a continuation-in-part of Ser. No. 213,184, Jun. 29, 1988, Pat. No. 4,917,708.

[51] Int. Cl.⁵ .................................................. A61B 5/08
[52] U.S. Cl. ................................... 128/718; 128/719; 128/725
[58] Field of Search ............... 128/719, 718, 725, 716, 128/726, 730, 205.12, 205.23, 205.24, 203.26, 204.17, 201.13; 73/861, 861.02, 861.03, 198, 200

[56] References Cited

U.S. PATENT DOCUMENTS

| | | | |
|---|---|---|---|
| 4,200,094 | 4/1980 | Gedeon et al. | 128/201.13 |
| 4,368,740 | 1/1983 | Binder | 128/718 |
| 4,917,108 | 4/1990 | Mault | 128/718 |
| 5,038,792 | 8/1991 | Mault | 128/718 |

Primary Examiner—David Isabella
Assistant Examiner—K. Reichle
Attorney, Agent, or Firm—Krass & Young

[57] ABSTRACT

A calorimeter for generating signals representative of the oxygen consumption of a subject over a test period includes a bidirectional volume flow sensor and a carbon dioxide scrubber connected to a mouthpiece. Interconnections are such that the air inhaled by the subject passes through the flow meter and the exhaled breath passes first through the carbon dioxide scrubber and then through the flow meter. The electrical output signals from the flow meter are provided to a microprocessor-based computer which integrates the volume differences between the inhaled gas, and the exhaled gas after the carbon dioxide has been removed from it, over the period of the test. Since the exhaled carbon dioxide essentially replaces the oxygen used by the subject during the test, this integral difference is a function of the patient's oxygen consumption. The use of a bidirectional flow meter results in a simple instrument that may be disposed after a single use to avoid the need for sterilization.

6 Claims, 1 Drawing Sheet 5,179,958

RESPIRATORY CALORIMETER WITH BIDIRECTIONAL FLOW MONITOR

CROSS REFERENCE TO RELATED APPLICATION

This application is a continuation-in-part of the U.S. Ser. No. 368,947 filed Jun. 23, 1989, now U.S. Pat. No. 5,038, which is a continuation-in-part of U.S. Ser. No. 213,184, filed Jun. 29, 1988, now U.S. Pat. No. 4,917,708, issued Apr. 17, 1990.

FIELD OF THE INVENTION

This invention relates to indirect calorimeters for measuring respiratory oxygen consumption and more particularly to such a calorimeter employing a bidirectional flow meter for measurement of the inhaled and exhaled gases and a $CO_2$ scrubber which removes $CO_2$ from the exhaled gas before it is passed through the flow meter to allow the computation of the difference between the inhaled gas volume and the volume of the scrubbed exhaled gas to calculate oxygen consumption.

BACKGROUND OF THE INVENTION

My U.S. Pat. No. 4,917,708, issued Apr. 17, 1990, discloses an indirect calorimeter, or oxygen consumption meter, which may be used to measure the resting energy expenditure of a subject. This measurement is important for determination of the proper caloric content for feedings of hospitalized patients and also is useful in connection with weight loss diets since the basal energy requirement may vary during the period of the diet. Similarly, knowledge of caloric expenditure and oxygen consumption during exercise are useful for cardiac rehabilitation and athletic training.

My previous patent discloses a calorimeter which utilizes a unidirectional flow meter operative to generate electrical signals proportional to the respiratory gases passing through it, a carbon dioxide scrubber operative to remove $CO_2$ from the exhaled gas and valving and conduits connecting the flow meter and the scrubber between a source of respiratory gases, which may be either the ambient air or some form of positive pressure ventilator, and a patient mouthpiece. The inhaled air has a negligible content of carbon dioxide and the exhaled gas contains lung-contributed carbon dioxide of essentially the same volume as the oxygen consumed by the subject. Accordingly, the difference in volumes between the inhaled and scrubbed exhaled gases passed through the flow meter provides an indication of patient's oxygen consumption. By integrating these differences over a test period, which may last for several minutes, an accurate measurement of the subject's oxygen consumption during the trial may be obtained.

SUMMARY OF THE INVENTION

The present invention is directed toward a metabolic rate measurement device which is substantially simpler than my previous design by virtue of use of a bidirectional volume flow sensor which eliminates the need for much of the valving and interconnection employed in my prior device as a result of the requirement for passing both the inhaled and scrubbed exhaled gases through the flow meter in the same direction. This simplicity results in more reliable operation, lower cost, and the potential for disposability after a single use, thus eliminating the need for sterilization when some or all of the components of the prior art calorimeters were used with a sequence of subjects.

In the calorimeters of the present invention the bidirectional flow meter is preferably connected directly to the source of inhaled gases, which may be room air or a positive pressure ventilating machine. After passing through the flow meter the inhaled gases are either passed directly to the subject's mouthpiece or to the mouthpiece through the carbon dioxide scrubber. The exhaled gases are passed first through the scrubber and then to the flow meter in an opposite direction from the inhaled gases.

The inhaled gases are preferably heated to essentially the same temperature as the exhaled gas before passage through the flow meter by a resistance heater or the like. In one embodiment of the invention, which will subsequently be disclosed in detail, the water vapor content of the inhaled and exhaled gases are substantially equalized by provision of a moisture absorbent in the form of an artificial nose, which passes inhaled respiratory gases after they have passed through the flow meter and provides exhaled respiratory gases to the flow meter after they have been passed through the scrubber.

In another embodiment of the invention a capnometer may be disposed in the flow path between the subject's mouthpiece and the carbon dioxide scrubber so that exhaled gases are passed through the capnometer before being scrubbed. The capnometer generates an electrical signal which is a function of the carbon dioxide gas concentration in the exhaled gases. The electrical output of the capnometer is provided to the computer which uses that signal along with the flow meter signal to generate a signal proportional to the ratio of carbon dioxide to consumed oxygen, or the Respiratory Quotient.

Other objectives, advantages and applications of the present invention will be made apparent by the following detailed descriptions of two preferred embodiments of the invention. The descriptions make reference to the accompanying drawings in which:

DETAILED DESCRIPTION OF THE PREFERRED EMBODIMENTS

Figure 1:
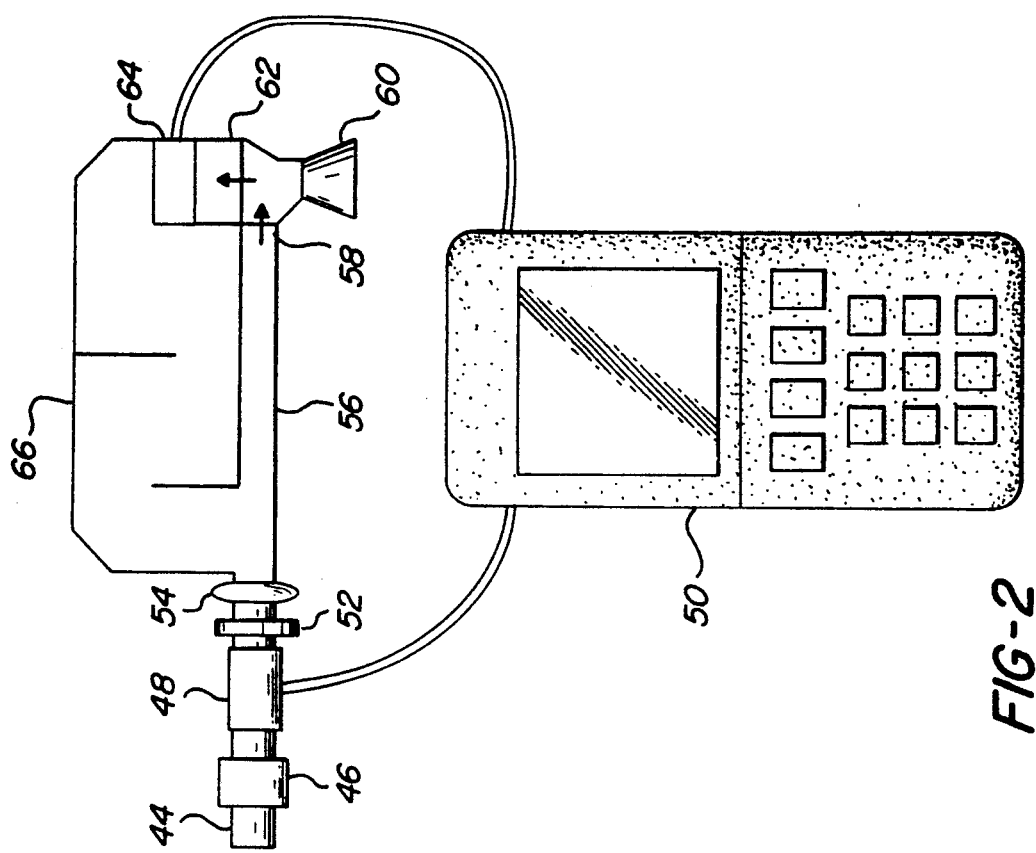
FIG. 1 is a schematic diagram of a first embodiment of my invention wherein the bidirectional flow meter is connected in series with a carbon dioxide scrubber and the patient mouthpiece so that both inhaled and exhaled gases pass through the scrubber and the inhaled gases pass through the flow meter in one direction before being scrubbed and pass through the flow meter in the opposite direction after being scrubbed.

The embodiment of the invention illustrated in FIG. 1, generally indicated at 12, employs a mouthpiece 14 adapted to engage the inner surfaces of the user's mouth so as to form the sole passage for inhaling and exhaling air passing through the mouth. A nose clamp of conventional construction (not shown) may be employed in connection with a mouthpiece 14 to assure that all respiratory gas passes through the mouthpiece. In alternative configurations a mask that engages the nose as well as the mouth might be employed or a endotracheal tube.

A conduit 16 connects the mouthpiece 14 to one end of a carbon dioxide scrubber 18. The scrubber 18 is a container having a central gas passageway filled with a carbon dioxide absorbent material such as sodium hydroxide or calcium hydroxide. Such absorbent materials may include sodium hydroxide and calcium hydroxide admixed with silica in a form known as "SODALYME." Another absorbent material which may be used is "BARALYME" which comprises a mixture of barium hydroxide and calcium hydroxide.

The other end of the scrubber is connected by a conduit 20 to an artificial nose 22 which constitutes a moisture-absorbing filter such as a filter formed of fibrous elements or a sponge. The artificial nose 22 acts to absorb water vapor from gases passing through it if the water vapor content of the gases is higher than the level of moisture contained in the filter or to add water vapor to the gases if the filter vapor level is higher than that of the gases.

The artificial nose 22 is connected via conduit 24 to a bacterial filter 26 which preferably traps particles of about 5 microns in size or larger. The conduit 28 connects the bacterial filter to a bidirectional flow meter 30. The flow meter is preferably of the pressure differential type such as manufactured by Medical Graphics Corporation of St. Paul, Minn. under the trademark "MEDGRAPHICS." Alternatively, other forms of bidirectional flow transducers might be used such as differential temperature types.

The other end of the flow sensor 30 is connected via conduit 32 to a resistance heater 34 which raises the temperature of air passing through it to approximately 37° C. Alternatively, the flow sensor might include means for measuring the temperature of the air exhaled by the subject and controlling the incoming air to that precise temperature.

The other end of the heater 34 is connected to an air intake/outlet 36 which may receive room air or may be connected to a positive pressure ventilator in the manner described in my patent application Ser. No. 368,947.

The electrical output signal from the flow meter 30 is provided to a microprocessor-based computation and display unit 38. The unit 38 converts the signal from the bidirectional flow sensor 30 to digital form, if it is an analog signal as employed in the preferred embodiment of the invention. Unit 38 is otherwise identical to the computation and display unit disclosed in my U.S. Pat. No. 4,917,718. It acts to integrate signals representing the difference between the inhaled and exhaled volume for the period of the test and sum these values and multiply them by a constant to arrive at a display of kilocalories per 24 hours. The keyboard 40 associated with the unit 38 allows storage and display of various factors in the same manner as the system of my previous patent.

In operation, assuming that room air is being inhaled, an inhalation by the subject on the mouthpiece 14 draws room air in through the intake 36 where it is first heated to essentially the temperature of the exhaled air by the heater 32. It then passes through the flow meter 30, generating a signal to the computation unit 38. After passing through the bacterial filter 28 and then the artificial nose 22, the inhaled air passes through the $CO_2$ scrubber 18. Since there is a negligible carbon dioxide content in room air the scrubber will have little effect upon inhaled air initially, but after prolonged use may add some water vapor to the incoming air by virtue of chemical reactions which occur when the subject exhales through the scrubber.

The inhaled air is then passed through the mouthpiece 14 to the subject. When the subject exhales, the exhaled air is again passed through the scrubber 18 in the opposite direction. The chemicals in the scrubber react with the carbon dioxide in the exhaled breath, producing water vapor and raising the temperature of the scrubber. The exhaled air is then passed through the artificial nose which tends to equalize the moisture vapor content of the exhaled air with that of the inhaled air. The exhaled air then passes to the flow meter 30 through the bacterial filter 26. The exhaled air will at this point have a water vapor content and temperature roughly comparable to that of the inhaled air so that the flow meter measurements of the inhaled and exhaled gases are on a comparable basis. The exhaled air then passes through the heater 34 to the air source.

The volume of exhaled air passed through the flow meter will be lower than the volume of inhaled air because of the absorption of the carbon dioxide by the scrubber 18. This difference in volume is a function of the oxygen absorbed from the inhaled air by the subject's lungs and the signals provided by the flow meter 30 to the unit 38 allow the integration and calculation of the resting energy expenditure in the manner described in my previous patent.

The system 12, unlike the devices disclosed in my previous patent, requires no one-way valves and is accordingly lower in cost and more reliable in operation than the previous devices. Its costs may be sufficiently low that the entire unit may be disposed of after a single test. Alternatively, since the bacterial filter 26 prevents bacterial contamination of the flow meter, the flow meter might be reused and the other components, to the right of the flow meter in FIG. 1, discarded after a single use.

Figure 2:
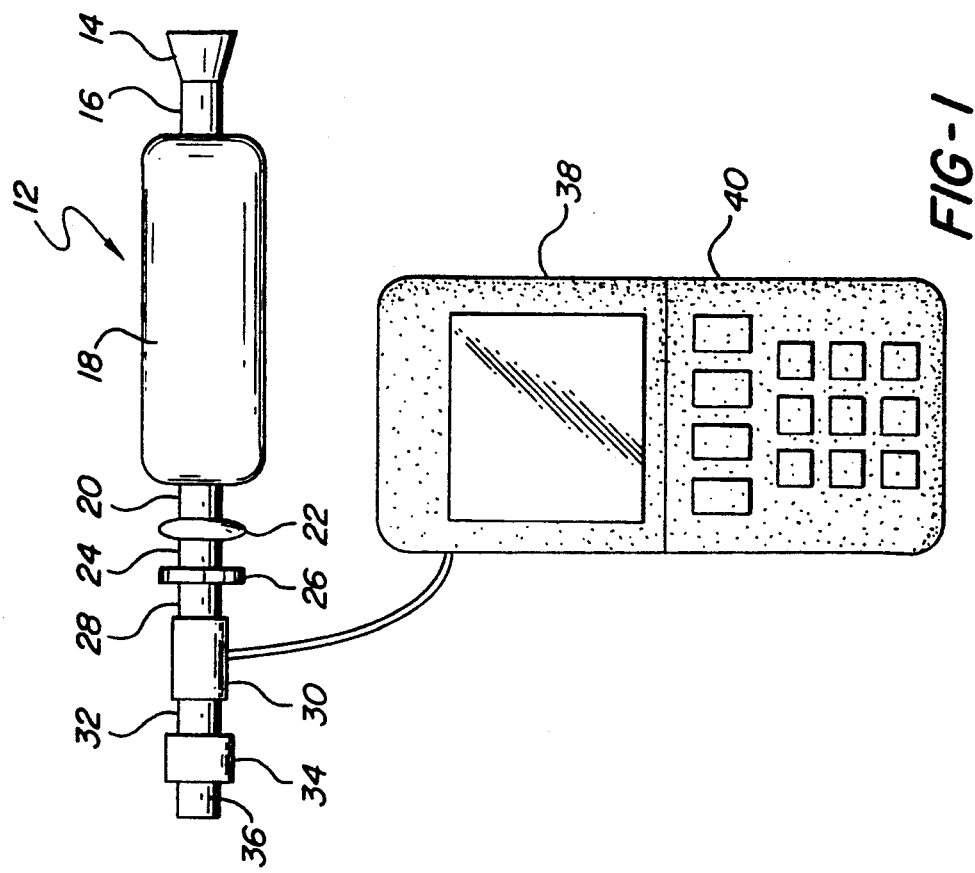
FIG. 2 represents an alternative embodiment of my invention employing a pair of one-way valves interconnected with the elements so that only the exhaled gases are passed through the scrubber and the inhaled gases are passed directly from the flow meter to the patient mouthpiece.

An alternative form of the invention, in which the inhaled gases are not passed through the carbon dioxide scrubber, and this eliminates any rebreathing problem is illustrated in FIG. 2. Again, a connection to an air source 44 passes inhaled air through a heater 46 and then to a bidirectional flow sensor 48. The electrical output of the flow sensor is provided to a microprocessor-based computation and display unit 50.

The inhaled air passes from the flow meter 48 through a bacterial filter 52 and then through a water vapor-absorbent artificial nose 54. It is then carried through conduit 56, through a one-way valve 58, to the subject mouthpiece 60.

The exhaled gases pass from the mouthpiece 60 through another one-way valve 62, which provides an exit from the mouthpiece, and through a capnometer sensor 64. The capnometer is operative to generate an electrical signal which is a function of the percentage of $CO_2$ concentration of the exhaled air volume which it passes. The capnometer may be of a convention type such as those described in U.S. Pat. Nos. 4,859,858; 4,859,859; 4,914,720; or 4,958,075. The electrical signal from the capnometer is provided to the microprocessor-based computer 232. In addition to calculating the oxygen consumption of the subject, $VO_2$, and the resting energy expenditure in kilocalories per unit time, the computer 232 generates a display of the exhaled $CO_2$ volume per unit time, the Respiratory Quotient (RQ), which equals $VCO_2$ divided by $VO_2$, and the resting energy expenditure. The Resting Energy Expenditure (REE) is preferably calculated from the Weir equation:

$$REE(KC/24 \text{ hours}) = 1440 \, (VO_2 * 3.341) + (VCO_2 * 1.11)$$

where $VO_2$ and $VCO_2$ are both measured in milliliters per minute.

A capnometer could similarly be provided in the calorimeter of FIG. 1 between the mouthpiece 14 and the scrubber 18.

The output of the capnometer 64 is provided to the $CO_2$ scrubber 66 which removes the $CO_2$ from the exhaled gases in the same manner as the scrubber 18 of the embodiment of FIG. 1 and provides its output to the flow passage 56. Since the flow path through the artificial nose 54, the bacterial filter 52, the flow meter 48, the heater 46, and the air inlet/outlet 44 has a lower resistance than the passage through the one-way valve 58 particularly while the subject is exhaling, the output from the scrubber takes this low resistance flow path and the exhaled volume again passes through the flow meter 48, in the reverse direction from the inhalation, and its output signal is provided to the computer 50. Since the passageway from the output of the scrubber 66 has a higher resistance to flow than the passage through the unidirectional valve 58, the inhaled air passes through the valve 58 to the mouthpiece rather than through the $CO_2$ scrubber in the reverse direction.

The embodiment of FIG. 2, by avoiding passage of the inhaled air through the scrubber, minimizes the volume of exhaled air that remains in the scrubber after an exhalation and is necessarily inhaled before air from the source 44 is inhaled, thereby removing any limitation on the size of the scrubber.

Having thus described my invention, I claim:

1. An indirect calorimeter operative to measure the respiratory oxygen consumption per unit time of a subject comprising:
    a respiratory connector operative to be supported in contact with the subject so as to pass inhaled and exhaled gases as the subject breathes;
    means for connecting to a source of respiratory gases;
    a pass-through bidirectional flow meter adapted to generate electrical signals as a function of the volume of gases which pass through it in either direction;
    a pass-through carbon dioxide scrubber operative to absorb carbon dioxide from gases which pass through it;
    conduits interconnecting said respiratory connector, said means for connecting to a source of respiratory gases, said scrubber and said flow meter so that upon inhalation by the patient gases are passed from the source of respiratory gases, through the flow meter, to the subject through the respiratory connector and upon exhalation by the subject the exhaled gases are passed first through the scrubber, then through the flow meter in a direction opposite to the inhaled gases; and
    means for receiving the generated electrical signal from the flow meter and for generating a signal proportional to the integral of the difference between the inhaled and exhaled gas volumes over a period of time.

2. The indirect calorimeter of claim 1 wherein the flow meter is of the pressure differential type.

3. The indirect calorimeter of claim 1 wherein the flow meter is of the temperature differential type.

4. The indirect calorimeter of claim 1 wherein said conduits are operative to cause the inhaled gases to be passed through the carbon dioxide scrubber after passing through the flow meter and before passing to the subject through the respiratory connector.

5. The indirect calorimeter of claim 1 including valve means connected to the conduits operative to pass inhaled gases directly to the subject through the respiratory connector from the flow meter and to pass exhaled gases through the carbon dioxide scrubber before they pass through the flow meter.

6. The indirect calorimeter of claim 1 further including a capnometer sensor interconnected so as to pass exhaled gases to the carbon dioxide scrubber, the capnometer being operative to generate an electrical signal proportional to the carbon dioxide concentration of gases which it passes, and connections between the capnometer and the means for receiving the generated electrical signal from the flow meter, said means for receiving the generated electrical signal additionally including means to generate a signal representative of the respiratory quotient of the subject.

* * * * *

UNITED STATES PATENT AND TRADEMARK OFFICE
CERTIFICATE OF CORRECTION

PATENT NO. : 5,179,958

DATED : January 19, 1993

INVENTOR(S) : James R. Mault

It is certified that error appears in the above-identified patent and that said Letters Patent is hereby corrected as shown below:

Column 1, Line 9, Delete "5,038," Insert --5,038,792--

Column 4, Line 42, Delete "this" Insert --thus--

Signed and Sealed this

Second Day of November, 1993

Attest:

BRUCE LEHMAN

Attesting Officer     Commissioner of Patents and Trademarks